US011573635B1

(12) United States Patent
Belkacem et al.

(10) Patent No.: US 11,573,635 B1
(45) Date of Patent: Feb. 7, 2023

(54) FACE MASK FOR ACCURATE LOCATION OF SENSORS RELATIVE TO A USERS FACE, A COMMUNICATION ENABLING FACE MASK AND A COMMUNICATION SYSTEM INCLUDING THE FACE MASK

(71) Applicant: United Arab Emirates University, Al Ain (AE)

(72) Inventors: Abdelkader Nasreddine Belkacem, Al Ain (AE); Fady Alnajjar, Al Ain (AE); Waleed Khalil Ahmed, Al Ain (AE); Bassam Walid Aljazzar, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 17/568,067

(22) Filed: Jan. 4, 2022

(51) Int. Cl.
*G06F 3/01* (2006.01)
*G01D 11/30* (2006.01)

(52) U.S. Cl.
CPC .............. *G06F 3/015* (2013.01); *G01D 11/30* (2013.01)

(58) Field of Classification Search
CPC .............. A61M 16/0633; A61M 16/06; A61M 16/0694; A61M 16/0683; A61M 16/0605; A61B 5/6803; A61B 5/282
See application file for complete search history.

(56) References Cited

U.S. PATENT DOCUMENTS

| | | | | |
|---|---|---|---|---|
| 3,451,748 A | * | 6/1969 | Halprin | G03B 35/24 352/38 |
| 8,082,124 B2 | | 12/2011 | Miyano et al. | |
| 8,082,149 B2 | * | 12/2011 | Schultz | G10L 15/24 704/235 |

(Continued)

FOREIGN PATENT DOCUMENTS

| | | |
|---|---|---|
| EP | 1423846 B1 | 3/2006 |
| JP | 2012146116 A | 8/2012 |

(Continued)

OTHER PUBLICATIONS

Matteo Stoppa and Alessandro Chiolerio, Wearable Electronics and Smart Textiles: A Critical Review, Sensors, 2014, 36 pages; vol. 14.

(Continued)

*Primary Examiner* — William Lu
(74) *Attorney, Agent, or Firm* — Boyle Fredrickson, S.C.

(57) ABSTRACT

Face mask communication system 100 includes face mask 10 worn by user 14 and signal receiving hand glove 16 worn by user 18. Glove 16 includes data receiver 66 for data communication with mask 10 and includes multiple vibrotactile devices for generating haptic signals. Mask 10 includes an elastic element of flexible material, and a plurality of EMG sensors 12 fixed to the element, for sensing electrical activity of face regions of the user's 14 face. Mask 10 includes a processor 60; decoding algorithm 110 and transmitter 62 for, respectively, processing signals from the sensors 12; generating command instructions based on the (Continued)

signals; and wirelessly transmitting the signals to receiver 66 of glove 16. Mask 10 includes thread elements connected to the elastic element of mask 10 enabling tensioning of the element to provide for fitment of mask 10 to users of different sizes, for optimal location sensors 12.

18 Claims, 12 Drawing Sheets
(6 of 12 Drawing Sheet(s) Filed in Color)

(56) References Cited

U.S. PATENT DOCUMENTS

| | | | |
|---|---|---|---|
| 8,165,698 | B2 | 4/2012 | Lehtoluoto |
| 8,300,010 | B2 | 10/2012 | Aviles et al. |
| 8,836,638 | B2 | 9/2014 | Madhvanath |
| 9,060,385 | B1 | 6/2015 | Manning |
| 9,784,257 | B1 * | 10/2017 | Liu .................. A41D 13/0155 |
| 9,911,358 | B2 | 3/2018 | Ghovanloo et al. |
| 10,521,014 | B2 | 12/2019 | Tadi et al. |
| 10,943,100 | B2 | 3/2021 | Tadi et al. |
| 2002/0095750 | A1 * | 7/2002 | Hammerslag ............ A43B 5/16 24/68 SK |
| 2003/0051732 | A1 * | 3/2003 | Smith ................ A61M 16/0633 128/206.27 |
| 2004/0071363 | A1 * | 4/2004 | Kouri ................ G06K 9/00516 382/128 |
| 2004/0163648 | A1 * | 8/2004 | Burton .............. A61M 16/0633 128/204.21 |
| 2005/0268916 | A1 * | 12/2005 | Mumford .......... A61M 16/0633 128/207.18 |
| 2010/0094366 | A1 * | 4/2010 | McCarthy ............. A61M 16/12 128/204.23 |
| 2010/0131268 | A1 | 5/2010 | Moeller |
| 2013/0047987 | A1 * | 2/2013 | Mays ................ A61M 16/0875 128/204.18 |
| 2014/0342324 | A1 | 11/2014 | Ghovanloo et al. |
| 2015/0151070 | A1 * | 6/2015 | Capra ............... A61M 16/0683 128/207.11 |
| 2015/0290415 | A1 * | 10/2015 | Dunn ................ A61M 16/0069 128/205.25 |
| 2015/0366504 | A1 * | 12/2015 | Connor ................ A61B 5/6804 600/301 |
| 2016/0354231 | A1 * | 12/2016 | Thornton ................ A61F 5/566 |
| 2016/0363997 | A1 | 12/2016 | Black et al. |
| 2017/0136264 | A1 * | 5/2017 | Hyde .................... G16H 50/30 |
| 2017/0143932 | A1 * | 5/2017 | McCarthy ........... A61M 16/204 |
| 2017/0199180 | A1 * | 7/2017 | Kobayashi ......... G01N 29/2462 |
| 2017/0212723 | A1 | 7/2017 | Atarot et al. |
| 2017/0274167 | A1 * | 9/2017 | Huddart ............ A61M 16/0866 |
| 2017/0361045 | A1 * | 12/2017 | Fu .................... A61M 16/0683 |
| 2018/0184975 | A1 * | 7/2018 | Kaasinen ............. A61B 5/0255 |
| 2019/0346925 | A1 * | 11/2019 | Daniels .................. G06F 3/013 |
| 2019/0377412 | A1 | 12/2019 | Parastegari et al. |
| 2020/0151934 | A1 * | 5/2020 | Rakshit ............. G06K 9/00496 |
| 2021/0282479 | A1 * | 9/2021 | Nagel ....................... A61L 9/16 |

FOREIGN PATENT DOCUMENTS

| | | | | |
|---|---|---|---|---|
| KR | 101810806 B1 | 12/2017 | | |
| WO | WO-2012122650 A1 * | 9/2012 | ............... | A42B 3/04 |
| WO | WO-2015022671 A1 * | 2/2015 | ............... | D04B 1/14 |
| WO | WO-2015196255 A1 * | 12/2015 | ......... | A61M 16/0051 |

OTHER PUBLICATIONS

B. Denby, T. Schults, K. Honda, Thomas Hueber, J.M. Gilbert, et al., Silent Speech Interfaces, Speech Communication, Elsevier: North-Holland, 2010, 52(4), pp. 270.

Yi-Hsiou Hsu, Exploring the Effect of Using Vibrate-Type Haptic Glove in the VR Industrial Training Task, KTH Royal Institute of Technology, Sweden 2020, 58 pages.

Public-Key Cryptography, Wikipedia, Jun. 1, 2021, 10 pages.

Daniel Shor et al., Designing Haptics: Comparing Two Virtual Reality Gloves with Respect to Realism, Performance and Comfort, IEEE International Symposium on Mixed and Augmented Reality Adjunct, Oct. 2018, 7 pages.

* cited by examiner

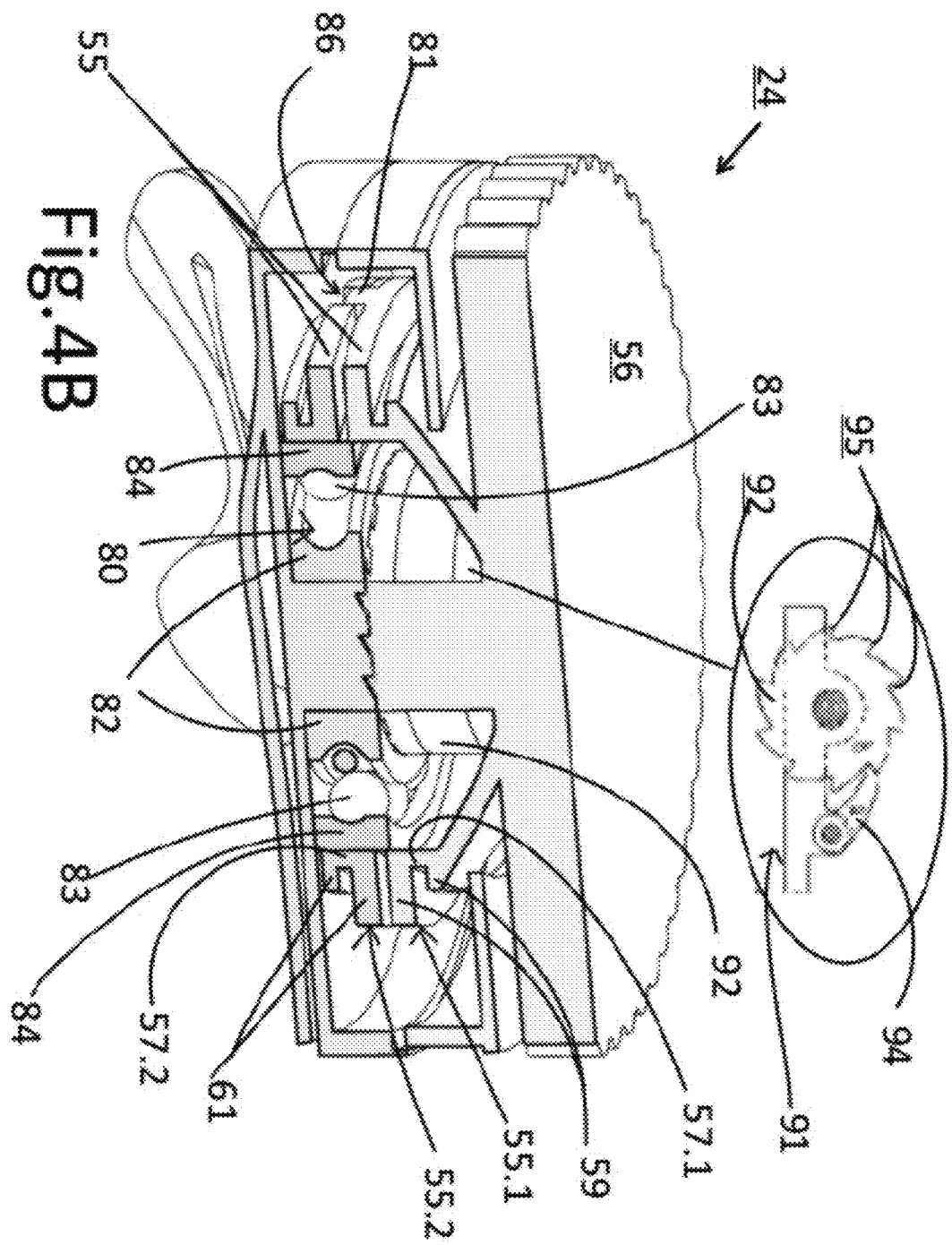

FACE MASK FOR ACCURATE LOCATION OF SENSORS RELATIVE TO A USERS FACE, A COMMUNICATION ENABLING FACE MASK AND A COMMUNICATION SYSTEM INCLUDING THE FACE MASK

FIELD OF INVENTION

This invention relates to a face mask for accurate location of sensors relative to a user's face. The invention relates further to a communication enabling face mask and to a communication system including the face mask. More particularly, the communication enabling face mask is configured to be worn by a user for enabling the user to engage in speechless communication.

BACKGROUND TO INVENTION

Surface electromyography (EMG) is a technique whereby voltage-measuring electrodes attach to the surface of the skin and are used to detect and/or infer various phenomena relating to muscle contraction.

EMG is presently used in research to estimate activity of muscle, in prosthetic design to provide a control signal, and in biofeedback to provide subjects with a visual or auditory indication of muscle contraction.

In practice, successful applications of EMG are unfortunately limited by the variability in signals detected and poor quality of estimates based on the detected signals. A major challenge to EMG based signal detection systems and applications is that EMG readings are adversely affected by a multitude of factors, especially repositioning of electrodes between subsequent sessions of EMG data collection. Other factors which effect accurate and consistent signal detection include ambient temperature, temperature of the user's skin and skin tissue properties of the user.

A need therefore exists for an accurate device for collecting EMG signals from a user, particularly during a series of subsequent sessions ordinarily necessitating repositioning of EMG sensors, at a beginning of each session. A need further exists for a device which can be used by users of different sizes, and which accurately and consistently detects EMG signal from the user, without lengthy and time consuming set-up and optimization of location of the EMG sensors relative to the user.

A need further exists for a so-called "silent/or speechless communication system" bases on obtaining EMG signals from a user and decoding these signals to produce meaningful instructions or feedback from the user.

In this specification, any reference to the terms "silent speech" and or "speechless communication", shall be interpreted broadly to mean, whispering, soft speech, as well as subvocalization and even so-called "mouthing words", whereby a person makes the correct mouth and tongue movements for speech, but without activation of the vocal cords and/or without making any noise.

SUMMARY OF INVENTION

According to a first aspect of the invention, there is provided a face mask for accurate location of sensors relative to a user's face, the face mask including:

an elastic mask element of flexible material which is configured to be worn on a face of the user and which is configured to at least partially cover a lower face region of the user's face, in use;

a plurality of sensors each fixedly located relative to the mask element, at different locations spaced apart from one another, for sensing electrical activity of predetermined associated underlying adjacent face regions of the user's face, when the face mask is worn by the user, in use;

the face mask being configured to be worn on the face of user's having different size faces, whereby the elastic properties of the elastic mask element and said fixed location of the sensors relative to the elastic mask element, in spaced arrangement relative to one another, enables fitment of the elastic mask element of the face mask to users of different sizes, in an arrangement providing optimal location of the sensors relative to predetermined adjacent underlying regions of the user's face.

Due to the fixed and spaced location of the sensors relative to the elastic mask element and due to the elastic properties of the mask element, the sensors are displaced, in use, a proportional distance apart from one another when the face mask is used by users having different face sizes, thereby to ensure, for user's having different face sizes, optimal location of the sensors relative to predetermined adjacent underlying regions of the user's face.

In a particular embodiment, the elastic mask element may be formed of (or may include) a woven material. The face mask may include a plurality of electrical wires, each one of which has an end region connected to an associated different one of the sensors. As such, the electrical wires may be woven into the weave of the woven material, so that said end regions of each wire are fixedly located relative to the flexible mask element, thereby to provide for said fixed location of the associated sensor relative to the flexible mask element.

In a particular embodiment, the face mask may comprise more than one layer. As such, the elastic mask element may constitute a first layer of the face mask. The face mask may include a second layer. The second layer may be formed of, or may include rigid or semi-rigid material for providing a desired degree of rigidity to the face mask. The second layer may include perforations to allow for aeration of the skin. The second layer may include a rigid or semi-rigid sheet element providing a predetermined degree of rigidity to the face mask.

In a particular embodiment, the second layer may constitute an inner layer while the first layer constitutes an outer layer The face mask may further include tensioning means for tensioning the elastic mask element, when the face mask is worn by the user, in use. The tensioning means may comprise an element tensioning system for tensioning the mask element on the user's face. The element tensioning system may include a plurality of thread elements, each thread element having a connected end which is connected to a particular region of the mask element, for tensioning the mask element when a tension force is applied to the thread element. The tensioning system may further include guiding means for guiding displacement of the thread elements, when the thread elements are tensioned.

More particularly, each guiding element may be in the form of a guide tube which is fixed to the mask element, at a predetermined location of the mask element. Each guide tube may provide for guided sliding displacement of the associated thread element relative to the guide tube. As such, the thread elements may be arranged in an arrangement wherein the thread elements extend through opposite open ends of one or more associated guide tubes, for guiding displacement of the thread elements when the thread elements are tensioned, in use.

In the embodiment wherein the elastic face element is formed of woven material, end regions of each thread element may be threaded through the weave of the woven material in a zig zag arrangement for fixing said end regions of the thread elements to the woven material of the mask element. More specifically, said zig zag arrangement ensures that a tensioning force applied to the thread element will be distributed across said region of the mask element through which the end region of the thread element is woven in said zig zag fashion.

The inventors have found that in this way, said threaded end region of each thread element defines a tensioning zone defined on the mask element, said tensioning zone corresponding with the region of the woven fabric of the mask element through which the thread element is woven in said zig zag fashion. As such, each thread element controls tensioning of the associated tensioning zone of the mask element. In use, the thread elements are arranged so as to create multiple tensioning zones adjacent to one another to provide for uniform tensioning of the mask element.

In a particular embodiment, each thread element may have an anchor formation secured to, or near, the fixed end of the thread element. The anchor formation may be configured for preventing the thread element from slipping through the weave of the woven material, when said tension force is applied to the thread element. The anchor formation may be formed of a piece of twisted wire having dimensions too large to fit through the weave of the woven material, when said tension force is applied to the thread element.

The tensioning system may further include tensioning means for tensioning the thread elements. The tensioning means of the tensioning system may be in the form of a thread tensioning system. The thread tensioning system may comprise one or more spool assemblies for tensioning the thread elements. The spool assembly or each spool assembly of the pair of spool assemblies may be configured for tensioning the thread elements on the associated one of the two opposite lateral sides of the face mask, in use. The spool assembly, or each spool assembly of the pair of spool assemblies may be rotatably mounted relative to the flexible mask element. More particularly, the spool assembly/each spool assembly may be located at a location adjacent the user's neck, in use. More specifically, the/each spool assembly may be fixed relative to one or more layers of the face mask at a location adjacent the nape of the user's neck, in use.

The/each spool assembly may include a barrel upon which the thread elements are wound, in use. The spool assembly/each spool assembly may further include a pair of opposite spaced flanges, each located at opposite ends of the barrel, for locating the thread elements relative to the barrel. The barrel of the/each spool assembly may include an arbor to provide for guided rotation of the barrel, in use, when the thread elements are wound onto the barrel.

The sensors may be in the form of Surface Electromyography (EMG) sensors for sensing electrical activity at the surface of the skin. As such, the EMG sensors may be configured for taking electrical measurements from the user's skin underlying each sensor. In use, the EMG sensors obtain voltage measurements from the user's skin which is used to detect and/or infer electrical signals within muscle tissue at said predetermined regions of the users face.

The sensors may be grouped into clusters of sensors. As such, each group of sensors comprise a plurality of sensors spaced apart from one another in a predetermined configuration. More particularly, each group of sensors are located relative to the mask element at a location wherein, when the face mask is fitted to the user, in use, each group of sensors is located at a particular pre-determined region of the user's face at which it is desired to obtain electrical measurements from the user's skin underlying the sensors. More specifically, each group of sensors may comprise sensors arranged in a quincunx arrangement.

The inventors have surprisingly found that said quincunx arrangement of sensors provides an accurate and reliable reading when the readings from each of the sensors constituting the quincunx of sensors is averaged. More specifically, the inventors have found that the average reading of said quincunx of sensors is particularly accurate at identifying muscle contraction in the region of the user's face underlying the quincunx of sensors.

In a particular embodiment, the face mask may further include a pair of head/neck-engaging segments, which surround a back region of at least one of the user's head and/or neck, in use. As such, each head/neck-engaging segment may include an opening to accommodate a user's ear, and through which the user's ear will extend, in use. More specifically, at least one of the head/neck-engaging segments may include mask securing means for securing the face mask to the user. The mask securing means may include at least one connecting formation defined at an end region of one or both of the head engaging segments, for connecting the head-engaging segments to one another. The mask securing means may be configured for releasably connecting the head engaging segments to one another.

The mask securing means may be adjustable to accommodate different sized users. More specifically, the mask securing means may be in the form of a strap on one of the head-engaging segments and a buckle on the other of the head-engaging segments. The strap and the buckle may be configured to permit adjustable fitment of the face mask to the user, in use.

In a particular embodiment, the face mask may be in the form of a communication enabling face mask, for enabling the user to engage in speechless communication. The communication enabled face mask may include the face mask as defined and described hereinabove, and may further include: at least one of signal receivers for receiving signals from the plurality of sensors; and a signal transmitter for transmitting processed or unprocessed signals received from the sensors; and a power supply for supplying electrical power to the sensors and said at least one of the signal receiver and signal transmitter.

In a particular embodiment, the communication enabling face mask may include said signal receiver and said signal transmitter.

The communication enabling face mask may further include a signal processor for processing signals received from the sensors. The signal processor may be configured for detecting silent speech of the user. More specifically, the inventors have found that said average reading of said quincunx of sensors is particularly accurate at identifying silent speech and facial expressions of the user.

According to another aspect of the invention, there is provided a communication system including:

at least one face mask as described and defined hereinabove, which is worn on a first user; and at least one signal receiving hand glove, which is configured to be worn on a hand of an additional user, the signal receiving hand glove including data receiving means and being in data communication with a signal transmitter of said at least one face mask for receiving data from the signal transmitter of said at least one face mask, said at least one signal receiving hand glove further including signal indicating means for indicating signals to the additional user in response to signals obtained from the signal transmitter of said at least one face mask.

The signal indicating means may include a visual display located on the hand glove. The visual display may be in the form of Light Omitting Diodes (LED) located on the hand glove. The LEDs may be located on a back region of the hand glove.

Alternatively, or additionally, the signal indicating means may include a haptic feedback device for providing haptic feedback to the additional user. The haptic feedback device may include a number of vibrotactile devices configured to produce a vibration detectable by the additional user. The vibrotactile devices may be located on the glove at locations corresponding with various predetermined regions of the fingers of the additional user and/or back of the hand of the additional user.

In a particular embodiment, the communication system may include a plurality of hand gloves, as described and defined hereinabove. The system may alternatively, or additionally, include a plurality of face masks as defined and described hereinabove.

The invention extends to the hand glove as described and defined hereinabove.

BRIEF DESCRIPTION OF DRAWINGS

The patent or application file contains at least one drawing executed in color. Copies of this patent or patent application publication with color drawing(s) will be provided by the Office upon request and payment of the necessary fee.

Further features of the invention are described hereinafter by way of a non-limiting example of the invention, with reference to and as illustrated in the accompanying schematic drawings. In the drawings:

FIG. 4B (main Figure) shows a fragmentary sectional view of a part of the face mask, sectioned along section lines A-A of FIG. 4A and FIG. 4B (Inset) shows a fragmentary top view of a part of the drawing of FIG. 4B (main Figure) showing hidden detail not visible in FIG. 4B (main Figure).

DETAILED DESCRIPTION OF THE DRAWINGS

Figure 1:
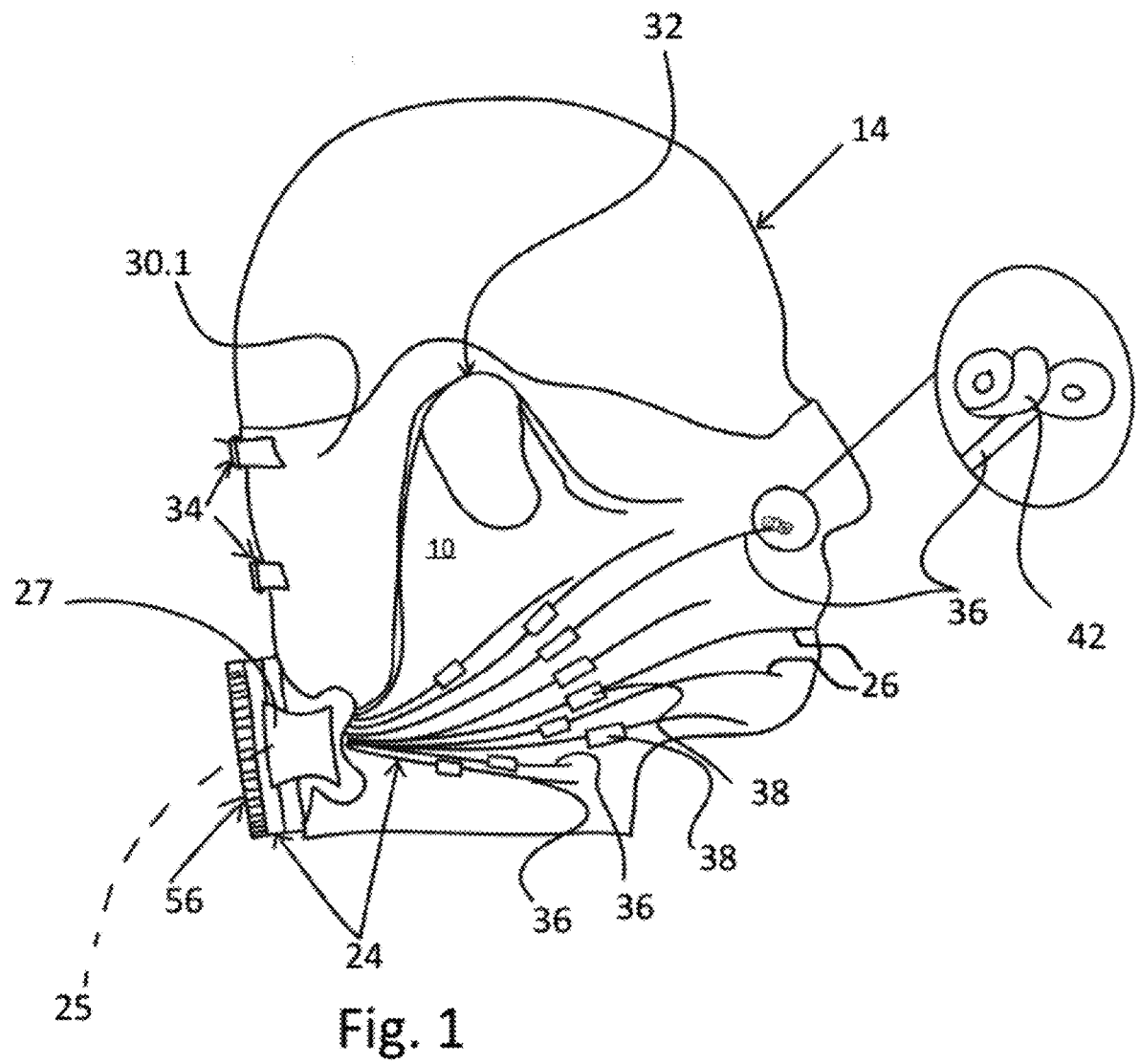
FIG. 1 shows a side view of a face mask, in accordance with one aspect of the invention, worn by a user, and an enlarged detail view of detail in FIG. 1 (in inset), the face mask constituting part of a communication system, in accordance with another aspect of the invention.

With reference to the drawings, a communication enabling face mask, in accordance with the invention is designated generally by the reference numeral 10. The communication enabling face mask 10 is configured for accurate location of sensors 12 relative to a user's 14 face for enabling the user to engage in communication, as will be explained in more detail hereinbelow.

Figure 8:
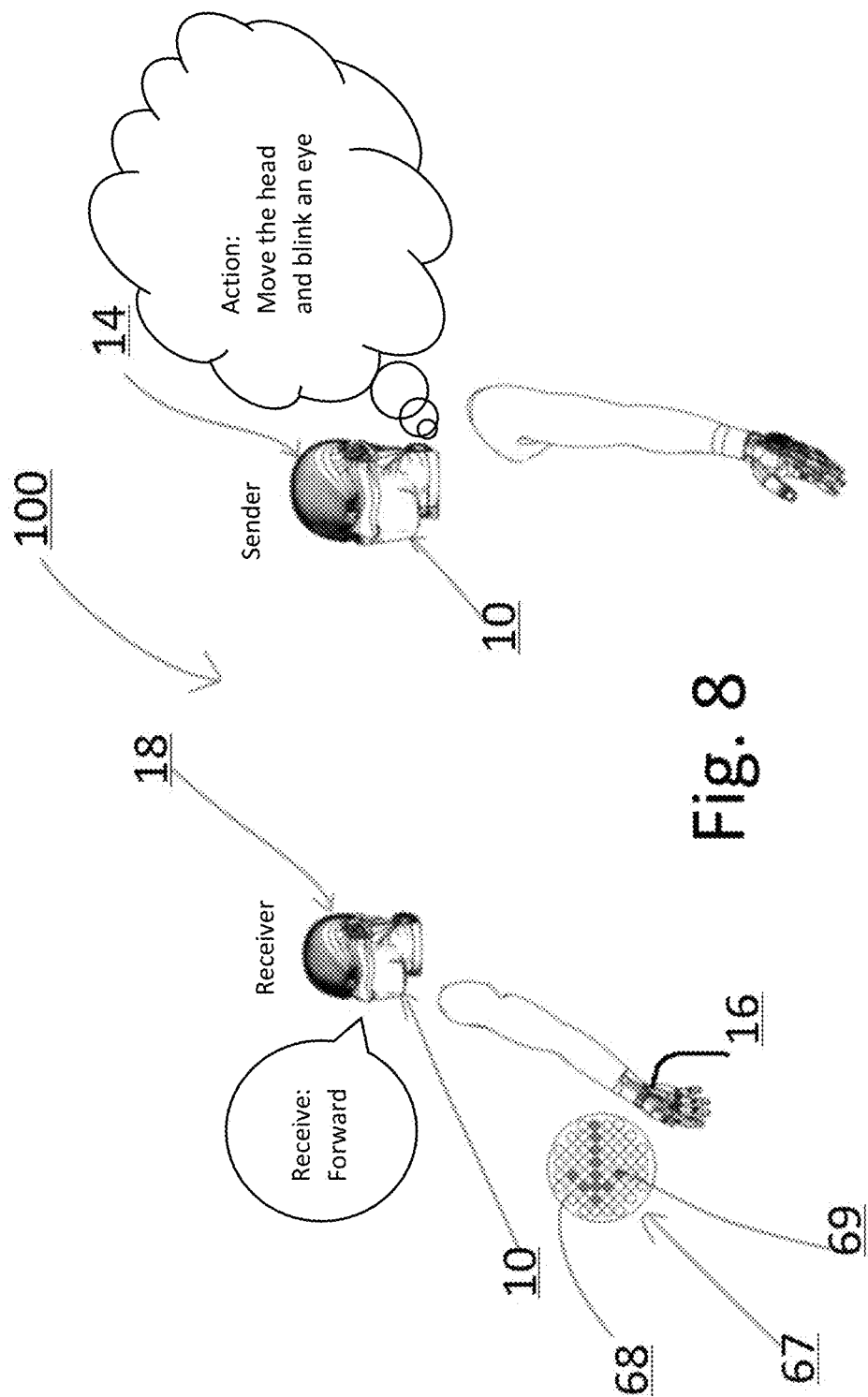
FIG. 8 shows a fragmentary perspective view of part of the communication system of FIG. 1.

The face mask 10 forms part of a communication system, in accordance with a second aspect of the invention, designated generally by the reference numeral 100 (shown in FIG. 8).

The face mask communication system 100 includes the face mask 10 which is worn on a first user 14, at least one signal receiving hand glove 16 which is worn by a second user 18, and which is in data communication with the face mask to provide for silent communication, as will be explained in more detail hereinbelow. The face mask communication system 100 further includes signal generating means in the form of earphones 19 for generating auditory signals, and signal indicating means for indicating signals, as will be explained below.

The face mask 10 includes a first layer comprising an elastic mask element 20 of flexible material (see FIG. 5), a second semi-rigid layer 22 (see FIG. 2) located beneath the mask element 20, plurality of Surface electromyography (EMG) sensors 12 each fixedly located relative to the mask element 20, at different locations spaced apart from one another, for sensing electrical activity of predetermined associated underlying adjacent face regions of the user's 14 face, when the face mask 10 is worn by the user 14, in use. The face mask 10 further includes tensioning means in the form of a tensioning system 24 for tensioning the mask element 20; a control system 25 and a housing 27.

The face mask 10 is configured to be worn on the face of user's having different size faces, whereby the elastic properties of the elastic mask element 20 and the fixed location of the sensors 12 relative to the elastic mask element 20, in spaced arrangement relative to one another, enables fitment of the elastic mask element 20 of the face mask 10 to users of different sizes, in an arrangement providing optimal location of the sensors 12 relative to predetermined adjacent underlying regions of the user's face. More specifically, due to the fixed and spaced-apart location of the sensors 12 relative to the mask element 20 and due to the elastic properties of the mask element 20, the sensors 12 are displaced, in use, a proportional distance apart from one another when the face mask 10 is used by users having different face sizes, thereby to ensure, for user's having different face sizes, optimal location of the sensors 12 relative to predetermined adjacent underlying regions of the user's 14 face.

The mask element 20 is of a woven fabric material and is configured to be worn on a face of a user so as to at least partially cover a lower face region of the user's face, in use, as illustrated in the drawings.

Figure 2:
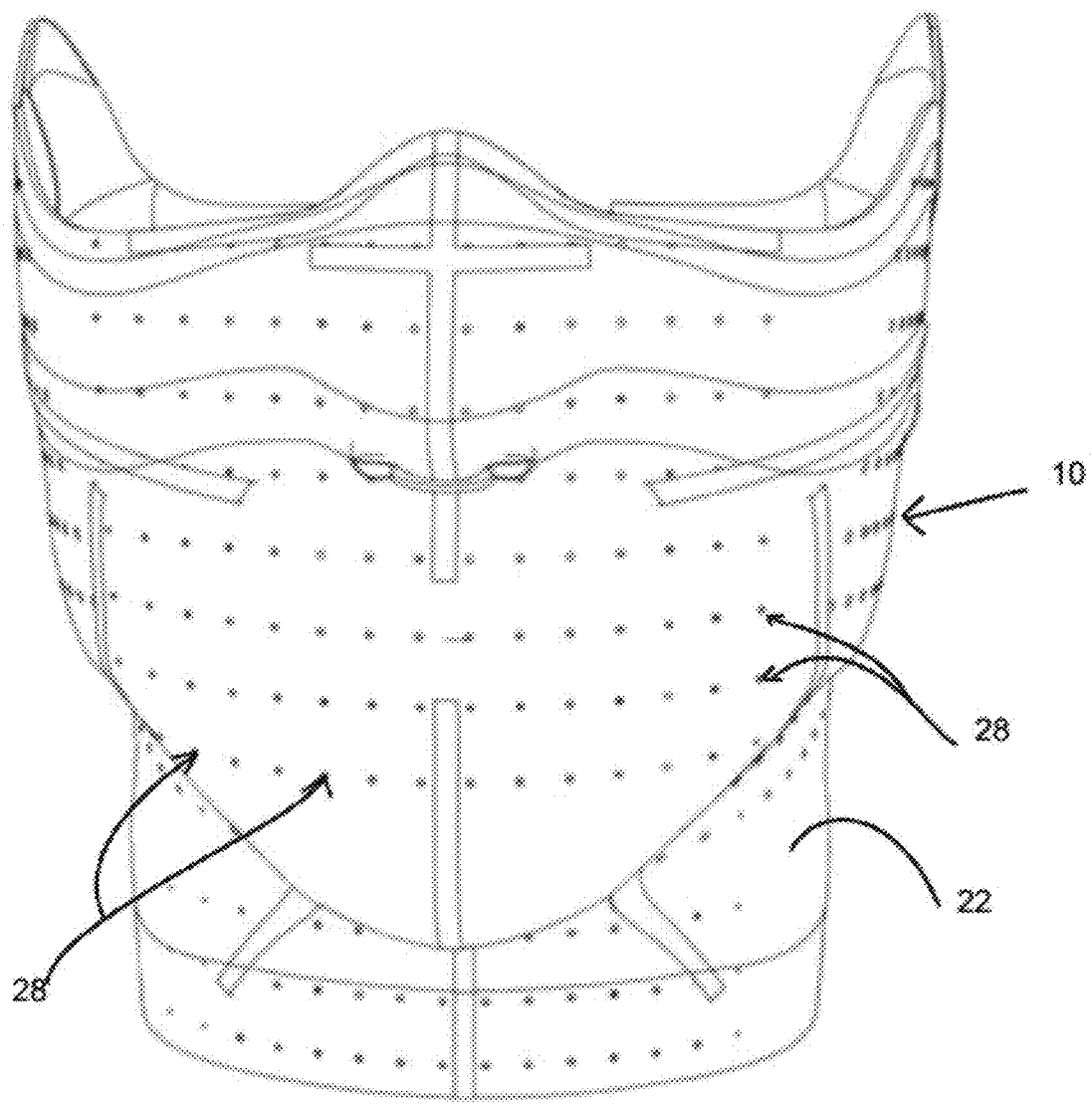
FIG. 2 shows a front view of one of the layers of the face mask of FIG. 1, the other layers of the face mask being omitted from the drawing.

The semi-rigid layer 22 is made of thin aluminium sheeting of less than 1 mm in thickness, the sheeting being highly electrically conductive to provide electrical conductivity between the sensors and the skin underlying the sensor, as will be explained below. The semi-rigid layer provides a predetermined degree of rigidity to the face mask 10 and includes perforations 28 defined therethrough as shown in FIG. 2 of the drawings. The perforations 28 allow for aeration of the skin for the purpose of air exchange to allow for heating and/or cooling of the skin of the user 14.

The mask element 20 and the semi-rigid layer 22 each include a pair of head/neck-engaging segments 30 which surround a back region of the user's head and neck, when the user 14 wears the mask, in use.

More specifically, each head/neck-engaging segment 30.1, 30.2 includes an opening 32 to accommodate the user's ear, and through which the user's ear will extend, in use. Each head/neck-engaging segment 30.1, 30.2 includes mask securing means for securing the face mask to the user. The mask securing means are in the form of a pair of complementary connecting formations, in the form of buckles and straps 34 defined at an end region of one of the head/neck engaging segments 30, for connecting the head-engaging segments 30.1, 30.2 to one another.

The buckles and straps 34 are adjustable to accommodate different sized users and permit snug fitment of the face mask 10 to a user's face.

Each EMG sensor 12 is configured for taking electrical measurements from the user's 14 skin underlying each sensor.

It will be understood that the sensors 12 are in contact with the thin aluminium sheeting constituting the semi-rigid layer 22. It will further be understood that the aluminium sheeting constituting the semi-rigid layer 22 is further in contact with the user's skin to provide for electrically conductivity between the sensors 12 and underlying regions of the user's skin.

In use, the EMG sensors obtain voltage measurements from the user's skin which is used to detect and/or infer electrical signals within muscle tissue at said predetermined regions of the users face.

Figure 7A:
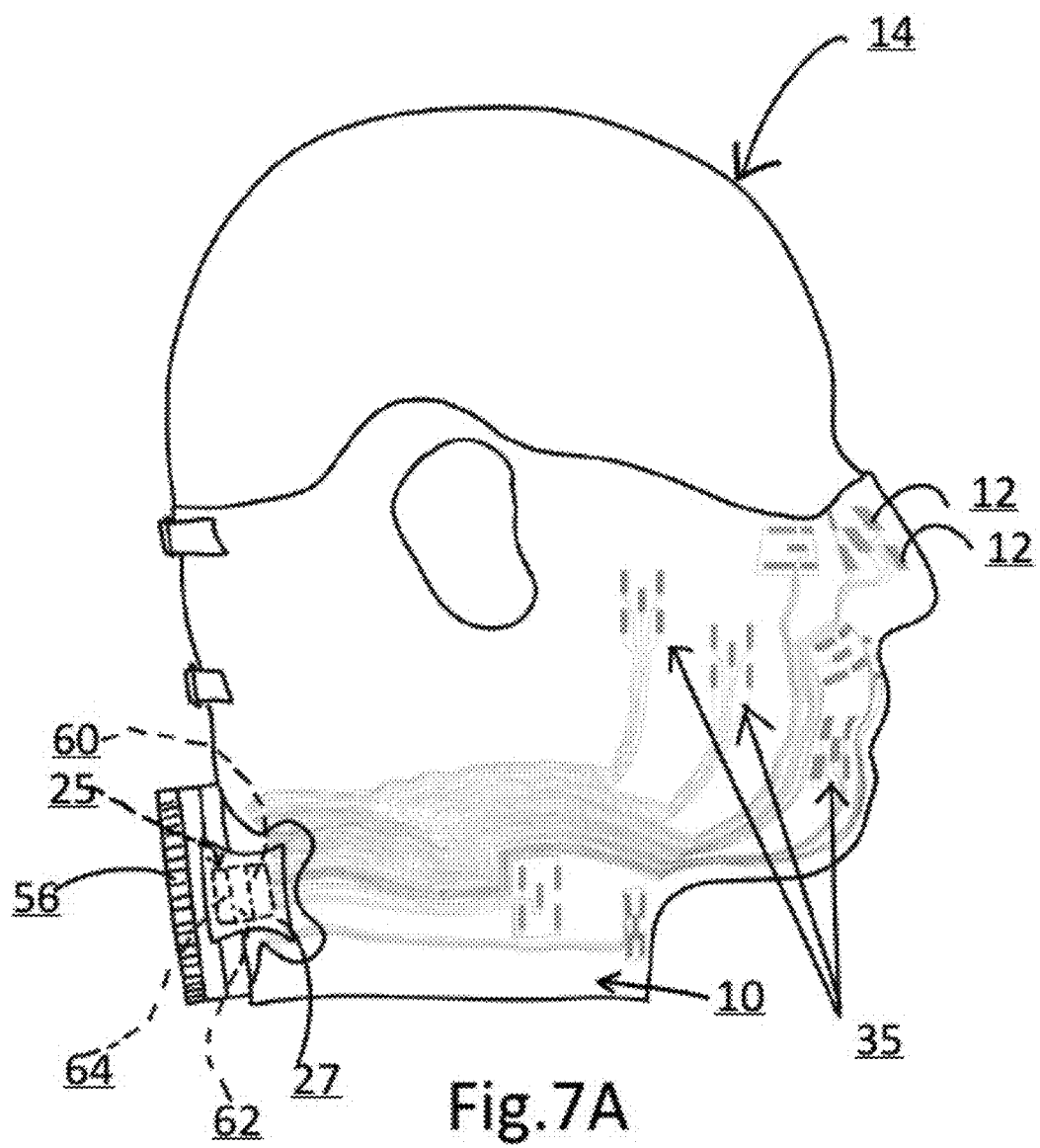
FIG. 7A shows a side view of the face mask of FIG. 1, showing the arrangement of sensors of the face mask.
Figure 7B:
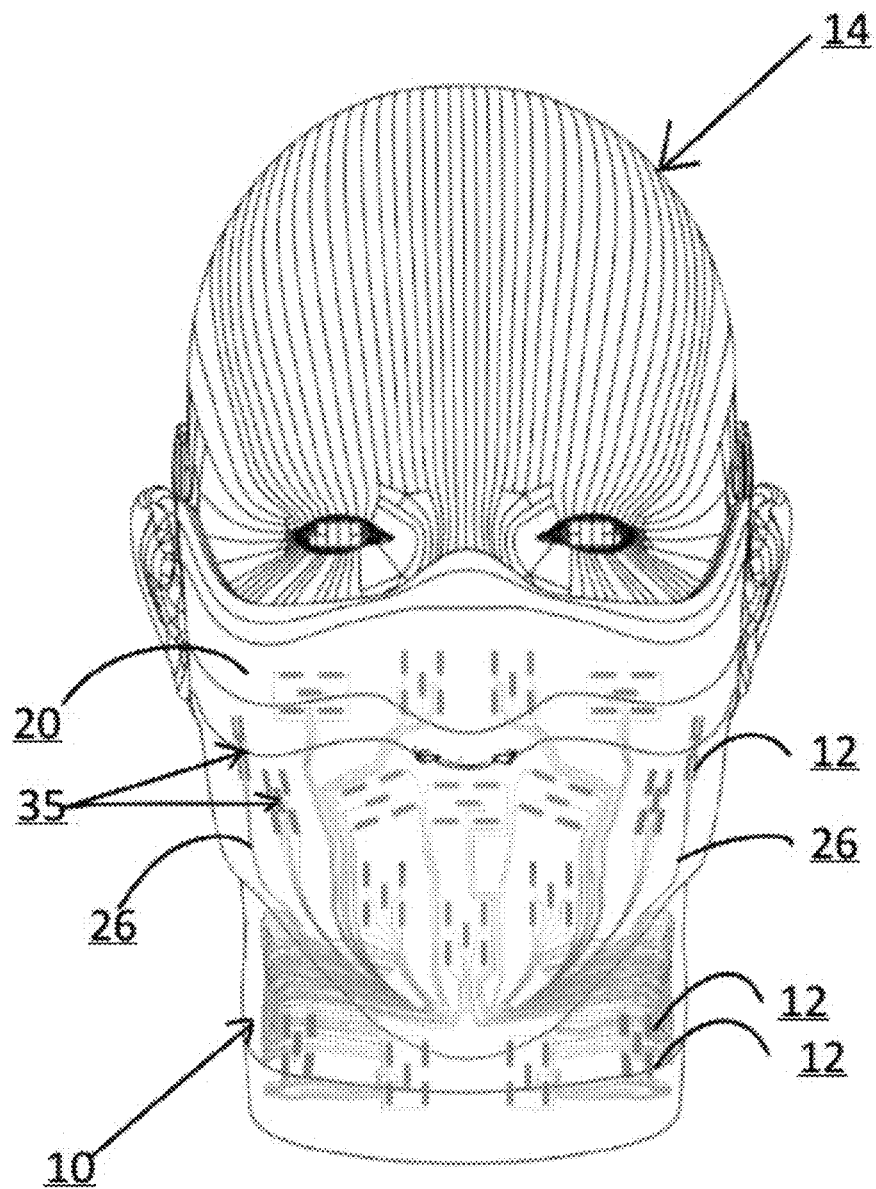
FIG. 7B shows a front view of the face mask of FIG. 1, showing arrangement of the sensors of the face mask.

The sensors 12 are grouped into clusters of sensors 12. As such, each cluster of sensors 12 comprise a plurality of sensors spaced apart from one another and arranged in a quincunx 35 arrangement, as illustrated in FIGS. 7A and 7B of the drawings.

More particularly, each cluster is located relative to the mask element 20 at a location wherein, when the face mask 10 is fitted to the user 14, in use, each cluster is located at a particular pre-determined region of the user's face at which it is desired to obtain electrical measurements from the user's skin underlying the sensors 12.

Figure 6A:
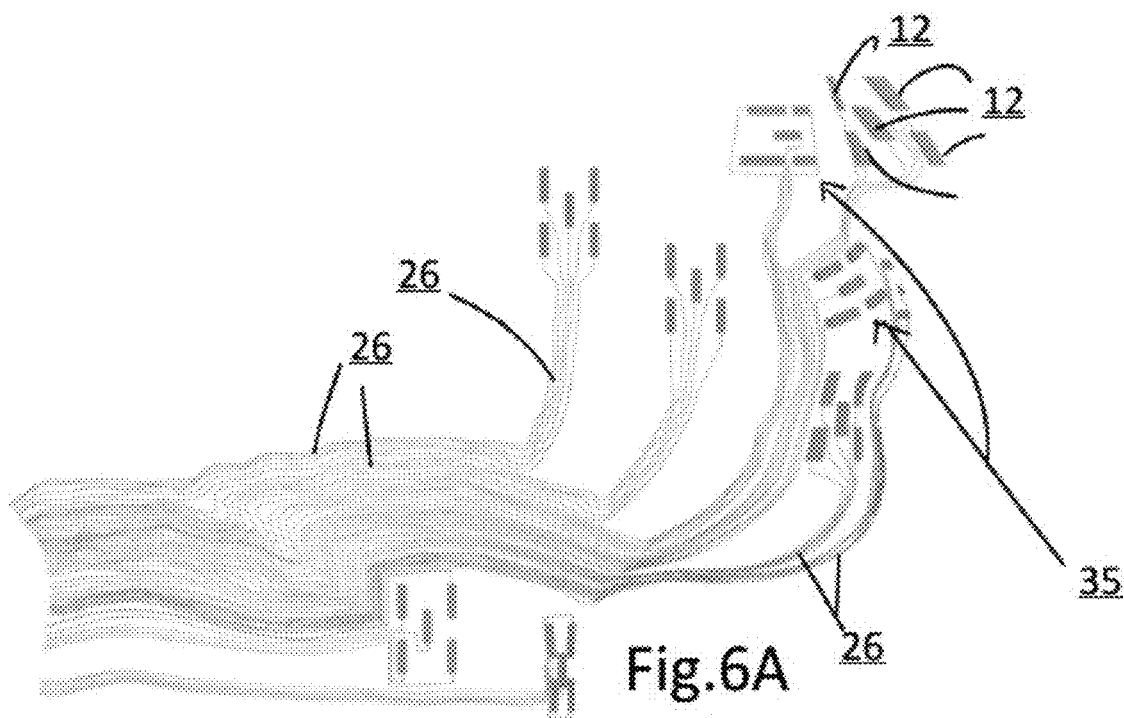
FIG. 6A shows a side view of location of sensors of the face mask of FIG. 1, with the face mask not shown for enhanced clarity.
Figure 6B:
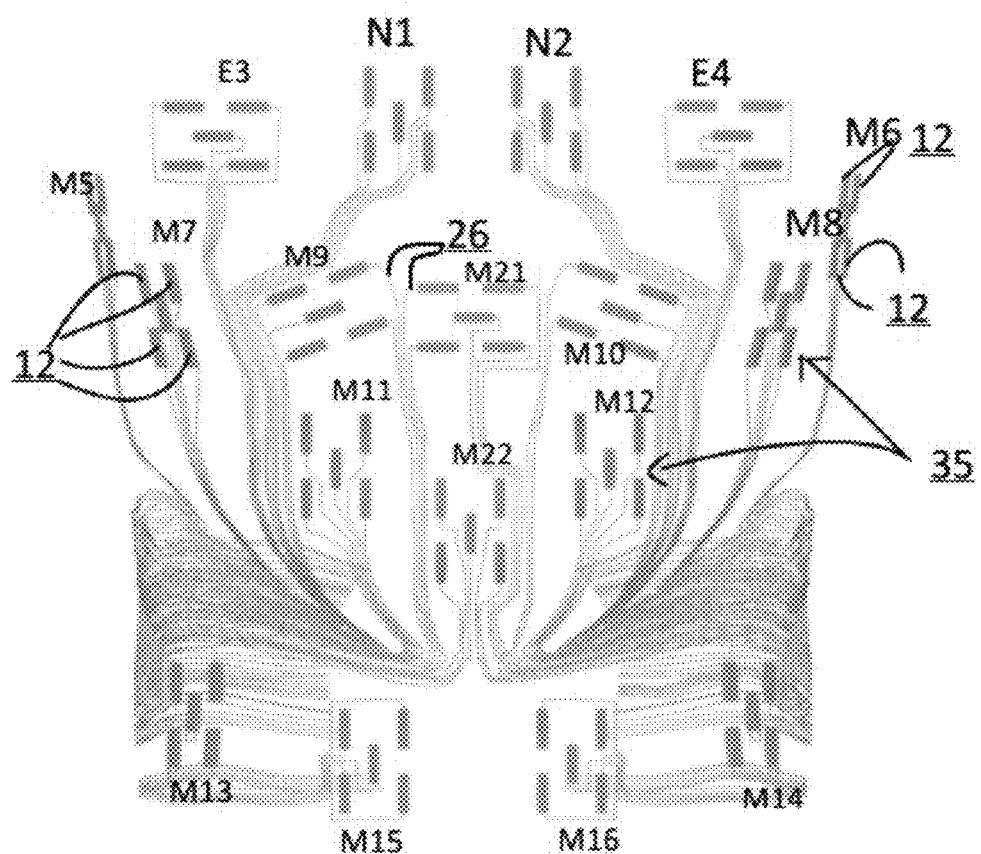
FIG. 6B shows a front view of the location of sensors of the mask of FIG. 1, with the face mask not shown for enhanced clarity.

More specifically, Table 1 below (read in conjunction with FIG. 6B of the drawings) show each cluster of sensors and associated actions/movements causing activation of the sensor.

TABLE 1

User actions and bi-interactions

Figure 5:
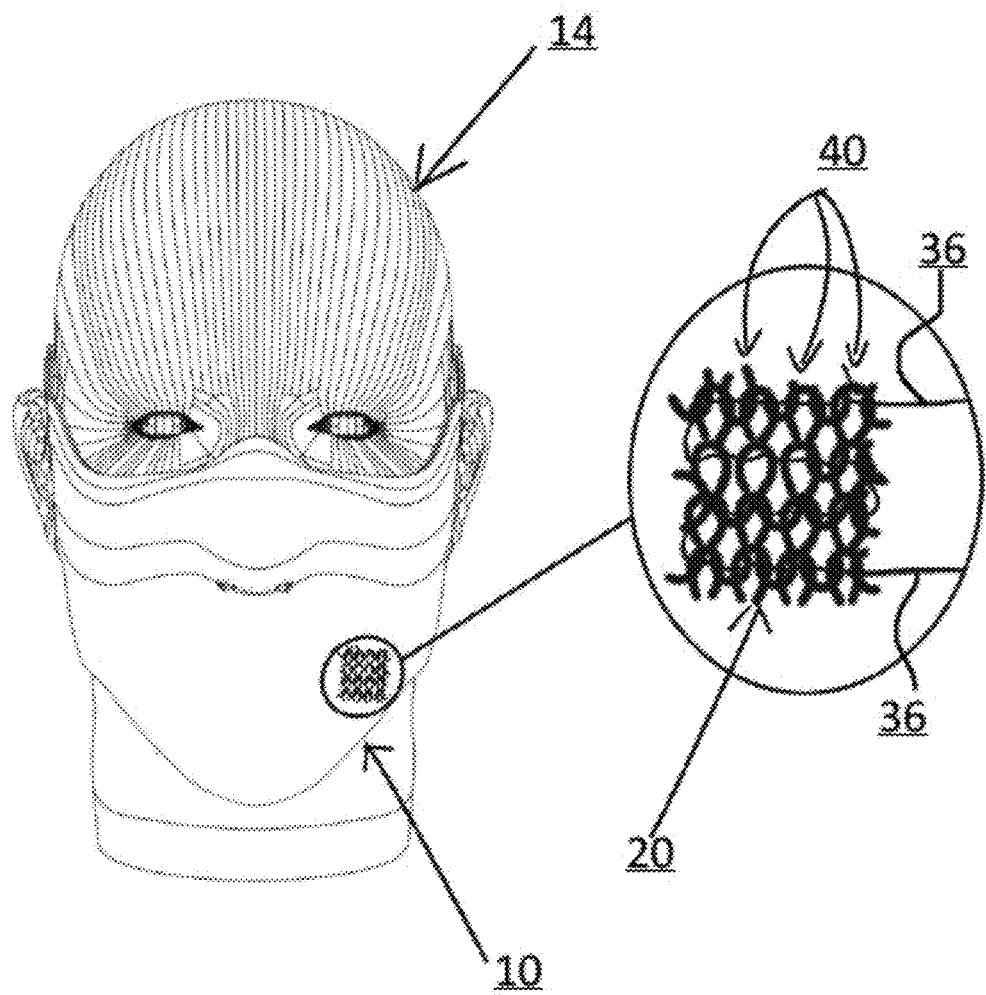
FIG. 5, shows a front view of the face mask of FIG. 1, with inset in FIG. 5 showing enlarged fragmentary detailed view of a weave of the facemask and wires of the sensors weaved into the weave of the face mask.

| Electrodes positions as indicated in FIG. 5 of the drawings | User Action | Instructions |
| --- | --- | --- |
| E3 | Right eye wink | Action 1 |
| E4 | Left eye wink | Action 2 |
| E3 and E4 | Eye blinking | Action 3 |
| N1 and N2 | Nose wrinkle | Action 4 |
| M13, M15, M16, and M14 | Head motion in X axis | Action 5 |
|  | Head motion in y axis | Action 6 |
| Sequence User Actions | | |
| M13, M15, and E3 | Head motion in X axis to right + right wink | Action 7 |
| M14, M16, and E4 | Head motion in X axis to left + left wink | Action 8 |
| M13, M15, and E3 | Head motion in X axis to right + left wink | Action 9 |
| M13, M15, and E3 | Head motion in X axis to left + right wink | Action 10 |
| E3, E4, Mz1, Mz2, M7, M9, M8, and M10 | Blink + smile | Action 11 |
| Mi + Ei + Ni | Facial-expression, (eye/head/lips) movements, and silent speech | Emotion recognition/speech decoding/commands |

In use, the inventors have found that approximately 10 to 15 clusters of sensors are ideal to monitor the users face and neck. By way of example, the clusters comprise two clusters on each side of the user's nose, four to six clusters around the lips and two to four clusters on the cheeks and two to four clusters on each side of the neck.

The inventors have surprisingly found that the quincunx 35 arrangement of sensors 12 provides an accurate and reliable reading when the readings from each of the sensors 12 constituting the quincunx 35 of sensors is averaged. More specifically, the inventors have found that the average reading of the quincunx 35 of sensors 12 is particularly accurate at identifying muscle contraction in the region of the user's 14 face underlying the quincunx 35 of sensors.

The element tensioning system 24 of the face mask 10 (for tensioning the mask element on the user's face) includes a plurality of thread elements 36; guiding means in the form of guide tubes 38 for guiding displacement of the thread elements 36, when the thread elements 36 are tensioned as explained below.

Each guide tube 38 is fixed to the mask element, at a predetermined location of the mask element 20. Each guide tube 38 provides for guided sliding displacement of the associated thread element 36 relative to the associated guide tube 38. As such, the thread elements 36 are arranged in an arrangement wherein the thread elements 36 extend through opposite open ends of one or more associated guide tubes 38, for guiding displacement of the thread elements 36, when the thread elements 36 are tensioned, in use.

Each thread element 36 has a connected end connected to a particular region of the mask element, for tensioning the mask element when a tension force is applied to the thread element. More particularly, as shown in FIG. 5, end regions of each thread element are threaded though the weave of the woven material constituting the mask element 20, for fixing the end regions of the thread elements 36 to the woven material of the mask element 20. The inventors have advantageously found that this zig zag arrangement ensures that a tensioning force applied to the thread element 36 will be distributed across the threaded region of the mask element 20 through which the end region of the thread element 36 is woven in said zig zag fashion.

The inventors have found that in this way, the threaded end region of each thread element 36 defines a tensioning zone 40 defined on the mask element 20, said tensioning zone 40 corresponding with the region of the woven fabric of the mask element 20 through which the thread element 36 is woven in said zig zag fashion. As such, each thread element 36 controls tensioning of the associated tensioning zone 40 of the mask element 20. In use, the thread elements 36 are arranged so as to create multiple tensioning zones 40 adjacent one another, to provide for uniform tensioning of the mask element 20.

As shown in FIG. 1, each thread element 36 has an anchor formation 42 secured to the fixed end of the thread element 36. The anchor formation 42 is configured for preventing the thread element 36 from slipping through the weave of the woven material, when said tension force is applied to the thread element 36. The anchor formation 42 is formed of a piece of twisted wire, the twisted wire having dimensions too large to fit through the weave of the woven material, when said tension force is applied to the thread element 36.

The thread tensioning system 24 comprises a control wheel 56, a pair of spool assemblies 55 for tensioning the thread elements 36; a rotation mechanism to provide for rotation of the spool assemblies 55, as will be explained below.

The control wheel 56 is configured for rotating the spool assemblies and can be actuated by the user for rotating the spool assemblies, for tensioning the thread elements, in use, when the control wheel 56 is rotated by the user 14, in use.

Each spool assembly 55.1, 55.2 of the pair of spool assemblies 55 is configured for tensioning the thread elements 36 on the associated one of opposite lateral sides of the face mask 10, in use.

Each spool assembly 55.1, 55.2 is rotatably mounted relative to the flexible mask element 20. More particularly, each spool assembly 55.1, 55.2 is located at a location adjacent the user's neck, in use. More specifically, each spool assembly 55.1, 55.2 is rotatably mounted relative to the flexible mask element 20 and the semi-rigid layer 22 of the face mask 10 at a location adjacent the nape of the user's neck, in use.

Each spool assembly 55.1, 55.2 includes a barrel 57.1, 57.2 upon which the thread elements are wound, in use. Each spool assembly 55.1, 55.2 further includes a pair of opposite spaced flanges 59, 61, respectively, each located at opposite ends of the barrel, for locating the thread elements relative to the barrel.

A key formation 81 is defined on one of the flanges 59 of the spool assembly 55.1 while a complementary lock formation 86 in the form of a recess is formed on one of the flanges 61 of the spool assembly 55.2, for receiving the key formation 81 therein, for reasons which will be explained herein below.

The rotation mechanism provides for guided unidirectional rotation of the barrel 57.1 and barrel 57.2, in use, when the thread elements are wound onto the barrel 57.1 and barrel 57.2. The rotation mechanism includes a bearing 80 and a locking assembly 91 for locking rotation of the bearing 80 in a reverse direction to provide for unidirectional rotation of the barrels 57.1, 57.2 of the spool assemblies 55.1, 55.2.

The bearing 80 comprises an inner race 82, an outer race 84 and ball bearings 83 captured between the inner race 82 and the outer race 84 to provide for smooth and low friction rotation of the inner race 82 relative to the outer race 84.

Figure 3:
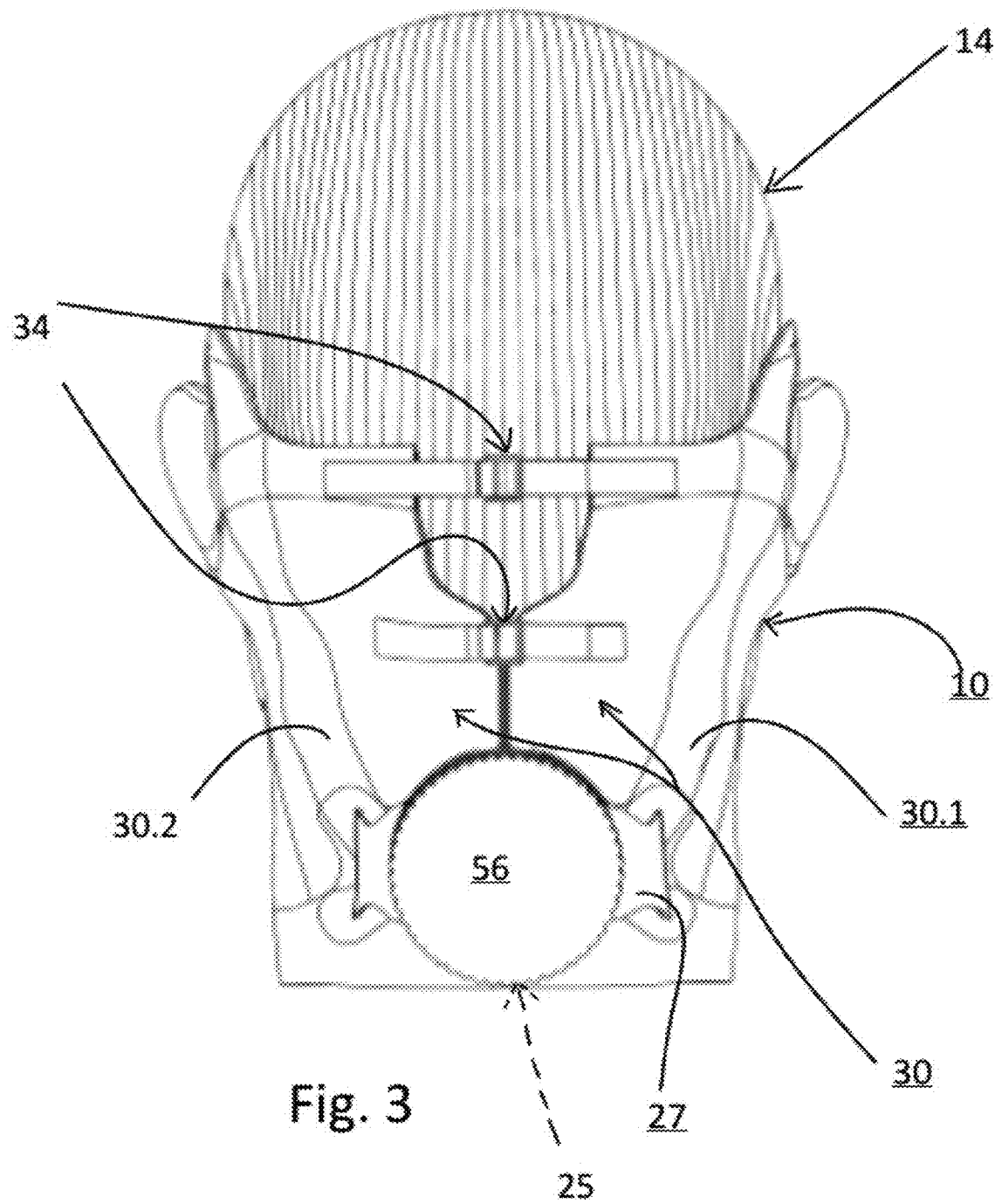
FIG. 3 shows a rear view of the face mask of FIG. 1 and the user wearing the mask.
Figure 4A:
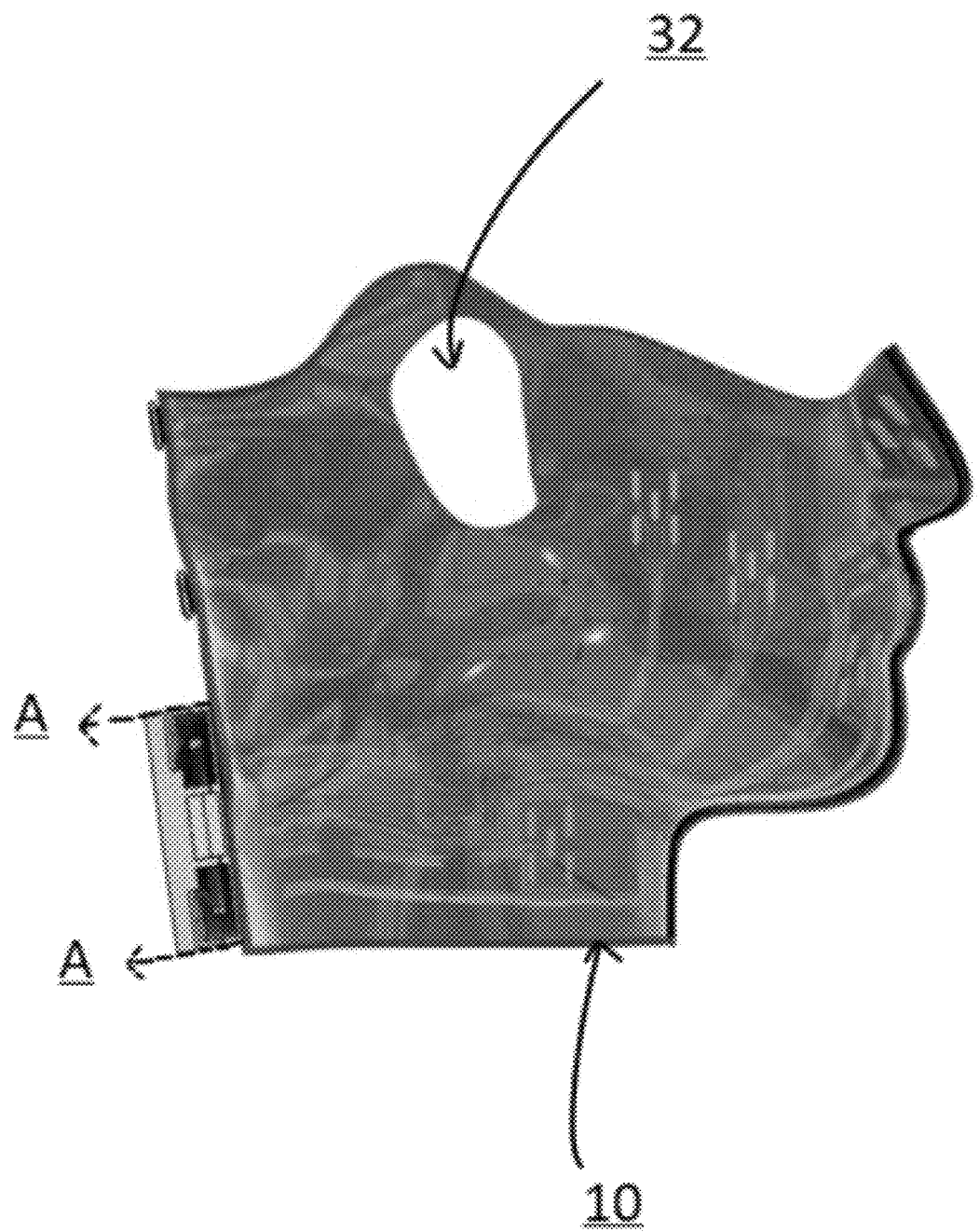
FIG. 4A shows another view of the mask of FIG. 1.

As best understood from FIG. 4B of the drawings, read in conjunction with FIG. 3 of the drawings, an operatively proximal portion the inner race 82 forms a tight frictional fit with housing 27 for securing the inner race 82 to the housing 27, which housing is fixedly connected to the face mask 10.

The barrel 57.2 of spool assembly 55.2 forms a tight frictional fit with the outer race 84 of the bearing 80.

Mechanical contact between the lock formation 86 defined on said one of the flanges 61 of the spool assembly 55.2 and the complementary key formation 81 defined on said one of the flanges 59 of the spool assembly 55.1, provides for locking rotation of the barrel 57.1 and the barrel 57.2 to one another such that the barrels 57.1 and 57.2 of the spool assemblies 55.1 and 55.2 rotate in unison when the control wheel 56 is rotated by the user, in use.

As such, the bearing 80 provides for rotation of the barrels 57.1, 57.2 of the spool assembly 55.1, 55.2 upon rotation of the control wheel 56 by the user. More particularly, in use, rotation of the control wheel 56 by the user, causes rotation of the barrels 57.1, 57.2 for winding the thread elements onto the barrel 57.1, 57.2, in use. It will be appreciated that thread elements from one side of the face mask are wound onto one of the barrels 57.1, 57.2 while the thread elements from the opposite side of the face mask are wound onto the other one of barrels 57.1 and 57.2.

The locking assembly 91 is illustrated in FIG. 4B of the drawings (see inset) and comprises a locking drum 92 which forms a tight frictional fit to an operative distal end of the inner race 82 and a sprung locking arm 94 for locking the locking drum 92 of the locking assembly 91 as will be explained below.

The locking drum 92 includes jagged teeth 95 which cooperate with the sprung locking arm 94 to provide for unidirectional rotation of the control wheel 56 and the barrels 57.1, 57.2. More specifically, the sprung locking arm 94 includes a spring (not shown) for biasing the locking arm into contact with the teeth 95 of the locking drum 92 (as illustrated in FIG. 4B of the drawings) to prevent clockwise rotation of the locking drum 92 relative to the sprung locking arm 94, but to permit anti-clockwise rotation of the locking drum 92, thereby to provide for said unidirectional rotation of the control wheel 56.

It will be understood that it is in fact the locking of the locking drum 92 which provides for tensioning of the thread elements as described hereinabove.

It will also be understood that when it is desired to remove the face mask 10, the sprung locking arm 94 can be displaced by the user out of contact with the teeth of the locking drum 92 when tensioning of the thread elements is no longer required, for example, when the user desires to remove the face mask 10. This will then permit the drum to be rotated in either direction, there to allow the thread elements to be wound off the barrels 57.1, 57.2 for releasing tension and allowing removal of the face mask.

Referring to FIG. 7A, of the drawings, the control system 25 includes a signal processor 60 for processing signals received from the sensors 12; a signal transmitter 62 for transmitting processed signals received from the signal processor 60; multiple electric wires 26; and a power supply 64 for supplying electrical power to the signal processor 60, and signal transmitter 62.

Each electric wire 26 has a first end connected to an associated different one of the sensors 12; and a second end connected to the signal processor 60; the purpose of which will be explained hereinbelow. As previously stated, the electrical wires 26 are woven into the weave of the woven material of the mask element 20, such that the end regions of each wire are thereby fixedly located relative to the flexible mask element 20, thereby to fixedly locate the associated sensor 12 relative to the flexible mask element 20.

As shown in FIG. 1 of the drawings, the housing 27 is mounted to the elastic mask element 20 and to the semi-rigid layer 22 at a location corresponding with the back of the user's neck, when the face mask is worn by the user, in use.

The signal processor 60, signal transmitter 62, power supply 64; and the pair of spool assemblies are all located within the housing 27.

The housing 27 is made up of two parts or housing halves which are magnetically connected to one another, this magnetic connection permits the face mask 10 to be easily removed and fitted to the user 14. More specifically, to fit the face mask, the user will locate the semi-rigid layer 22 upon the users face and magnetically connect each half of the housing to one another. Removal of the face mask entails separating the halves of the housing from one another.

Figure 9:
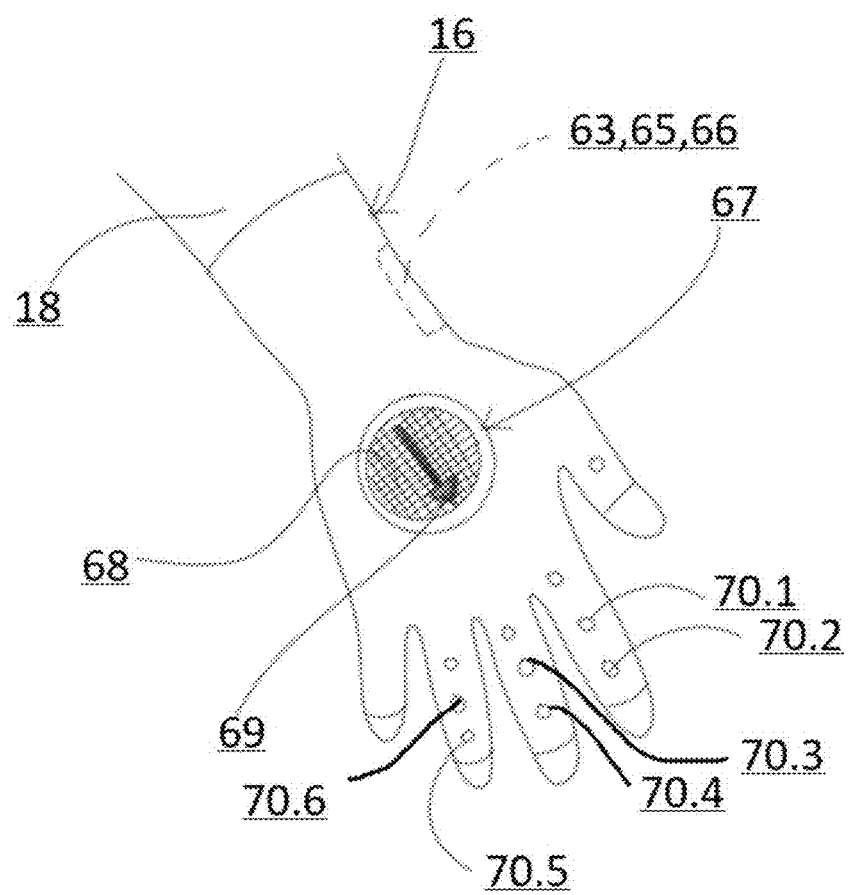
FIG. 9 shows an isometric view of a glove of the communication system of FIG. 1.

Referring to FIGS. 8 and 9 of the drawings, the signal receiving hand glove 16 of the communication system 100 shown in FIGS. 8 and 9 of the drawings includes a power supply, 63, a processor 65 and data receiving means in the form of a data receiver 66 which is in data communication with the signal transmitter 62 of face mask 10 for receiving data from the signal transmitter 62 of the control system 25 of the face mask 10. The power supply 63 is configured for supplying electrical power to the data receiver 66 and the processor 65 of the signal receiving hand glove 16.

The signal receiving hand glove 16 further including signal indicating means, in the form of a visual signal generator 67, and a tactile signal generator in the form of haptic feedback vibrotactile devices 70.1, 70.2, 70.3, 70.4, 70.5, 70.6 (and others, not labelled), for generating visual and tactile signals, respectively, for indicating signals obtained from the face mask 10.

The visual signal generator 67 includes a visual display located on the hand glove, in the form of a Light Omitting Diode (LED) display 68. The LED display 68 is located on a back region of the hand glove 16. The haptic feedback vibrotactile devices 70.1, 70.2, 70.3, 70.4, 70.5, 70.6 (and others, not labelled) are located on an outer side of the glove 16 for providing haptic feedback to the user 18. More particularly, the vibrotactile devices 70.1, 70.2, 70.3, 70.4, 70.5, 70.6 are located on the glove at locations corresponding with various predetermined regions of the fingers of the user 18 and/or back of the hand of the user 18.

Figure 10:
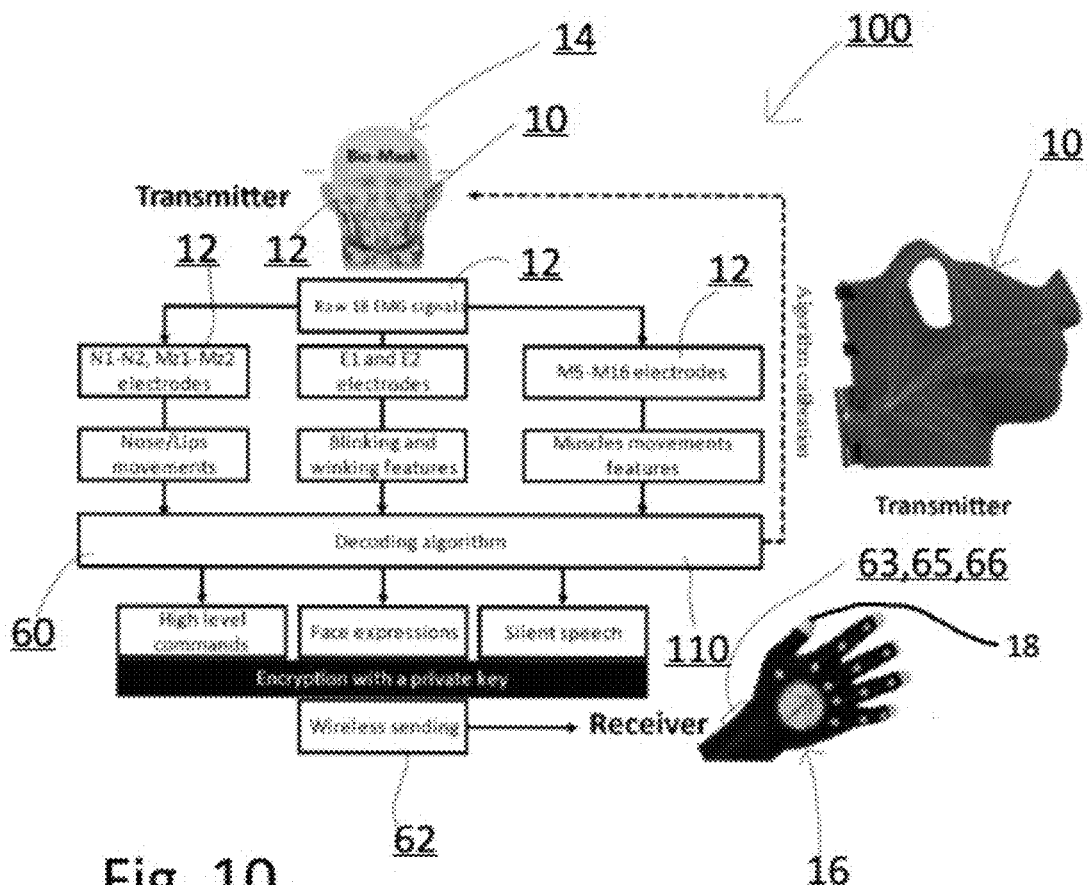
FIG. 10 shows a diagrammatic flowchart of the use of the communication system.
Figure 11:
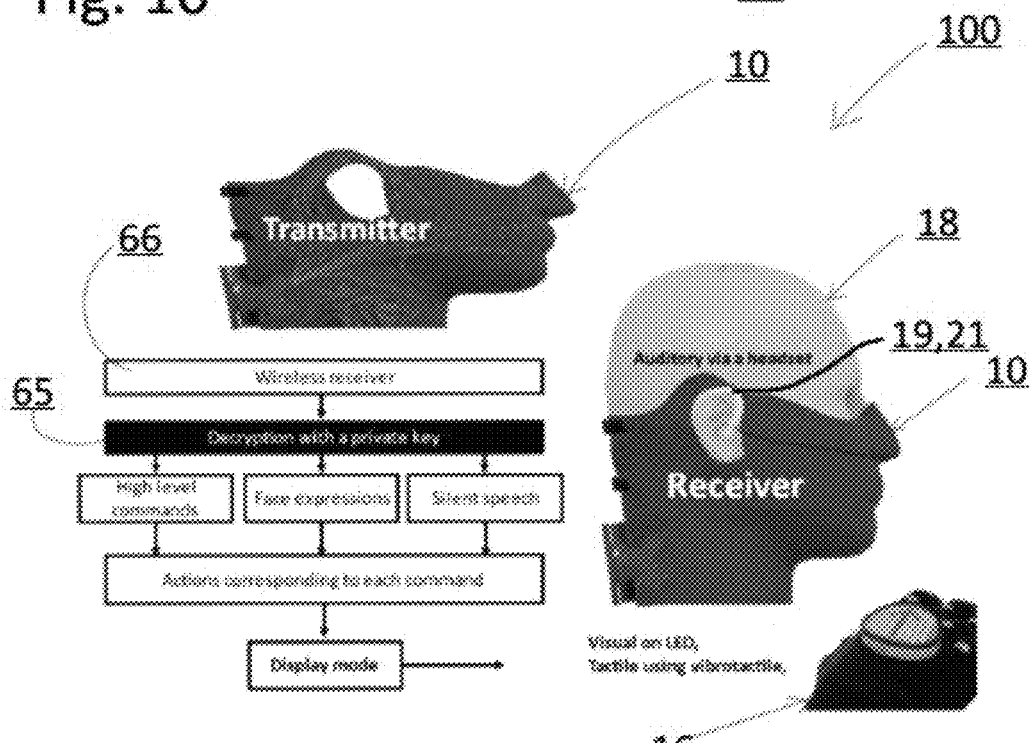
FIG. 11 shows a diagrammatic flowchart showing further steps of the use of the communication system.

Referring to FIGS. 10 and 11 of the drawings, an example of the operation of the communication system 100, in use, is provided.

Signals from the EMG sensors 12 are received by the decoding algorithm 110 of the signal processor 60. The signal processor 60 processes and interprets the signals using a decoding algorithm 110 of the signal processor 60 and specifically detects high level commands, facial expressions, and silent speech. More specifically, the sensors 12 detect actions of the user 14 including silent speech, facial expressions, and gestures (for example, winking, rapid blinking of the eyes of the user 14). Examples of detected actions are further set out in Table 1.

The decoding algorithm 110 generates a command signal/instruction which is encrypted on the signal processor 60 with a private key. The command signal/instruction is then sent wirelessly from the signal transmitter 62 of the control system 25 of the face mask 10 to the data receiver 66 of the hand glove 16.

As illustrated in Table 1, command signals/instructions are relayed, in use, in response to detection of a particular facial action performed by the user 14. In this way, a specific action, for example, silent speech, facial expression, or gesture, of the user 14 results in a repeatable and predetermined instruction being issued by the user, which is sent by the signal transmitter 62 of the control system 25 of the facemask 10 to the receiver 66 of the hand glove.

It will be appreciated the decoding algorithm 110 can thus be programmed by a user such that a predetermined particular facial action (silent speech, facial expression, or gesture or other face muscle contractions) performed by the user 14 corresponds with and results in a predetermined and desired instruction sent by the signal transmitter 62 of the control system 25 of the facemask 10 to the receiver 66 of the hand glove 16.

More specifically, the decoding algorithm 110 and the data receiver 66 and the processor 65 of the signal receiving hand glove 16, can thus be programmed by a user such that a predetermined particular facial action (silent speech, facial expression, or gesture or other face muscle contractions) performed by the user 14 corresponds with and results in a predetermined and previously agreed signal, such as activation of particular one or more of the haptic feedback vibrotactile devices 70.1, 70.2, 70.3, 70.4, 70.5, 70.6 located on an outer side of the glove 16, in response to specific signals which are sent by the signal transmitter 62 of the control system 25 of the facemask 10 to the receiver 66 of the hand glove.

In this manner, the face mask 10 is a communication enabling face mask, enabling silent and data secured communication between the user 14 and the second user 18.

The inventors have found that the encrypted command signal/instruction ensures that the all encrypted commands transmitted from the signal processor 60 can only be decrypted by the private key, by the data receiver 66 of the hand glove 16, thereby to ensure secure and private communication between the users 14 and 18. As such, the inventors envisage that the communication system 100 is ideal for various applications, such as, for example, the medical field, military and interactive entertainment.

The inventors envisage that the LED display 68 comprises a plurality of LED lights arranged in an equi-spaced arrangement so as to define a matrix of LED lights. The matrix of LED lights can thus be used to display signs, such as arrows 69, letters, etc, for sending pre-agreed signals from the user 14 to the additional user 18.

Similarly, if desired, auditory signals can be sent to the earphones 19.

The inventors have specifically found that due to this quincunx 35 arrangement of sensors 12, the mask 10 is sufficiently robust to put on and take off in a hurry and is still able to operate effectively, even with poor fitment. More specifically, even if fitment is less than ideal, the face mask 10 is able to detect the muscle and eye movements and translate these under difficult conditions, for example, stressful/combat situations.

In use, the inventors have found that the arrangement described hereinabove is particularly advantageous because, as previously mentioned, average reading obtained from each cluster of sensors comprising five sensors arranged in the quincunx 35 arrangement, is particularly accurate at identifying silent speech and facial expressions of the user, even when the face mask is less than ideally fitted.

Furthermore, the inventors have found that the elastic properties of the flexible mask element 20 and fixed location of the sensors 12, in spaced arrangement, enables fitment of the flexible mask element 20 to users of different sizes, for optimal location of the sensors relative to the user's face.

Advantageously, the inventors have found that the flexible mask element 20 expands uniformly when worn on the face of users of different sizes and because each sensor 12 is located by an associated electric wire 26, which is woven into the fabric constituting the flexible mask element 20, each sensor 12 is also fixedly located relative to the portion of mask element 20 through which the wire 26 is located. Therefore, when the mask element 20 expands (uniformly) to fit the face of different users, each sensor 12 is displaced a proportionate distance apart from one another such that the sensors are optimally located for faces of different sizes. The inventors have advantageously found that this arrangement maintains proportionate distances of the sensors 12 from one another, when worn by users having different sized faces, thereby to enhance the reliability of readings received from the sensors 12.

The element tensioning system 24 of the face mask 10 also provides for fast tensioning of the flexible mask element 20 under hurried, stressful or combat situations, where it is necessary to fit the face mask fast and accurately to the user's face.

In use, the inventors have found that it is highly advantageous that the thread elements 36 are arranged so as to create multiple tensioning zones adjacent one another to specifically provide for uniform tensioning of the mask element 20.

In a particular embodiment (not shown), the communication system includes a plurality of hand gloves, as described and defined hereinabove. The system may alternatively, or additionally, include a plurality of face masks, as defined and described hereinabove. In a particular embodiment (not shown), the face mask communication system may include additional face masks and additional gloves.

The inventors envisage that the communication system 100 may comprise a single sender or commander (user of the face mask 10) and one or group of receivers (additional users such as user 18).

The inventors also envisage that the earphones 19 may be useful for generating auditory signals and may include a built-in receiver 21 such that the earphones can receive data directly from the signal transmitter 62 of the control system 25 of the facemask 10, such that the earphones 19 can be utilized without the hand glove 16.

As such, it will be appreciated the decoding algorithm 110 can thus be programmed by a user such that a predetermined particular facial action (silent speech, facial expression, or gesture or other face muscle contractions) performed by the user 14 corresponds with and results in a predetermined and desired instruction sent by the signal transmitter 62 of the control system 25 of the facemask 10 to the receiver 66 of the hand glove, and/or to the receiver 21 of the earphones 19, for sending an auditory signal to the earphones 19.

In this manner, the face mask is a communication enabling face mask, enabling silent communication between the user 14 and the second user 18.

The invention extends to the hand glove as described and defined hereinabove.

What is claimed is:

1. A face mask for accurate location of sensors relative to a user's face, the face mask including:
    an elastic mask element of flexible material which is configured to be worn on a face of the user and which is configured to at least partially cover a lower face region of the user's face, in use;
    a plurality of sensors each fixedly located relative to the mask element, at different locations spaced apart from one another, for sensing electrical activity of predetermined associated underlying adjacent regions of the user's face, when the face mask is worn by the user, in use;
    the face mask being configured to be worn on the face of user's having different size faces, whereby the elastic properties of the elastic mask element and said fixed location of the sensors relative to the elastic mask element, in spaced arrangement relative to one another, enables fitment of the elastic mask element of the face mask to users of different sizes, in an arrangement providing optimal location of the sensors relative to said predetermined associated underlying adjacent regions of the user's face, with which the sensors are associated;
    wherein the flexible mask element expands uniformly when the face mask is fitted to users having different size faces and wherein said uniform expansion ensures that the sensors are displaced a proportionate distance apart from one another, such that the sensors are optimally located for faces of different size.

2. The face mask as claimed in claim 1, wherein the elastic mask element includes a woven material.

3. The face mask as claimed in claim 2, wherein the face mask includes a plurality of electrical wires, each one of which has an end region connected to an associated different one of the sensors.

4. The face mask as claimed in claim 3, wherein the electrical wires are woven into the weave of the woven material, so that said end regions of each wire are fixedly located relative to the flexible mask element, thereby to provide for said fixed location of the associated sensor relative to the flexible mask element.

5. The face mask as claimed in claim 2, wherein the face mask further includes tensioning means for tensioning the elastic mask element, when the face mask is worn by the user, in use.

6. The face mask as claimed in claim 5, wherein the tensioning means comprise an element tensioning system for tensioning the mask element on the user's face, the element tensioning system including a plurality of thread elements, each thread element having a connected end which is connected to a particular region of the mask element, for tensioning the mask element when a tension force is applied to the thread element.

7. The face mask as claimed in claim 6, wherein the tensioning system further includes guiding means including one or more guiding elements for guiding displacement of the thread elements, when the thread elements are tensioned.

8. The face mask as claimed in claim 7, wherein each guiding element is in the form of a guide tube which is fixed to the mask element, at a predetermined location of the mask element, each guide tube providing for guided sliding displacement of the associated thread element relative to the guide tube.

9. The face mask as claimed in claim 6, wherein end regions of each thread element are threaded through the weave of the woven material in a zig zag arrangement for fixing said end regions of the thread elements to the woven material of the mask element.

10. The face mask as claimed in claim 9, wherein said zig zag arrangement ensures that a tensioning force applied to the thread element will be distributed across said region of the mask element through which the end region of the thread element is woven in said zig zag fashion.

11. The face mask as claimed in claim 10, wherein each thread element has an anchor formation secured to, or near, the fixed end of the thread element for preventing the thread element from slipping through the weave of the woven material, when said tension force is applied to the thread element.

12. The face mask as claimed in claim 11, wherein the tensioning system further include tensioning means for tensioning the thread elements, the tensioning means of the tensioning system being in the form of a thread tensioning system comprising one or more spool assemblies for tensioning the thread elements, the or each spool assembly including a barrel upon which the thread elements are wound, in use.

13. The face mask as claimed in claim 12, wherein the tensioning system comprises a pair of spool assemblies, each spool assembly of the pair of spool assemblies are configured for tensioning the thread elements on the associated one of the two opposite lateral sides of the face mask, in use.

14. The face mask as claimed in claim 1, wherein the sensors are in the form of Surface Electromyography (EMG) sensors for sensing electrical activity at the surface of the skin.

15. The face mask as claimed in claim 14, wherein the sensors are grouped into clusters of sensors, each cluster of sensors comprise a plurality of sensors spaced apart from one another in a predetermined configuration.

16. The face mask as claimed in claim 15, wherein each group of sensors are located relative to the mask element at a location wherein, when the face mask is fitted to the user, in use, each group of sensors is located at a particular pre-determined region of the user's face at which it is desired to obtain electrical measurements from the user's skin underlying the sensors.

17. The face mask as claimed in claim 16, wherein each group of sensors comprises sensors arranged in a quincunx arrangement.

18. The face mask as claimed in claim 17, wherein an average reading of said quincunx of sensors provides for accurate readings of muscle contraction in the region of the user's face underlying the quincunx of sensors.

* * * * *